US005764340A

United States Patent [19]
Hofeldt

[11] Patent Number: 5,764,340
[45] Date of Patent: Jun. 9, 1998

[54] PORTABLE DEVICE FOR EVALUATION OF BINOCULAR VISION PROBLEMS

[76] Inventor: Albert J. Hofeldt, 200 E. 57th St., New York, N.Y. 10022

[21] Appl. No.: 692,051
[22] Filed: Aug. 2, 1996
[51] Int. Cl.$^6$ .................................. A61B 3/08; A61B 3/02
[52] U.S. Cl. .......................... 351/201; 351/239; 351/240
[58] Field of Search ................................ 351/239, 240, 351/241, 242, 243, 246, 237, 238, 201

[56] References Cited

U.S. PATENT DOCUMENTS 4,863,258  9/1989  Greene ..................................... 351/240

Primary Examiner—Hung X. Dang
Attorney, Agent, or Firm—Graham & James LLP

[57] ABSTRACT

A vision evaluation device which measures the three vision parameters of stereoscopic vision, fusion testing, and fusion recovery measurement. The device comprises a stereo-pair of images in constant view through the eye pieces of a lighted View Master® slide viewer. Two viewers are utilized, with the viewers using identical "4-Dot" stereo pairs but differing in that the right and left images are transposed. A reel mount in the View-Master viewer is mounted with a graded series of neutral density filters, with the filters being arranged so that the filter density increases over one eye as the reel is advanced with a lever, until the color of the solid circle changes. Use of the two viewers permits ready identification of an eye with nerve conduction defect, with one viewer measuring right eye defects and the other measuring left eye defects.

12 Claims, 3 Drawing Sheets

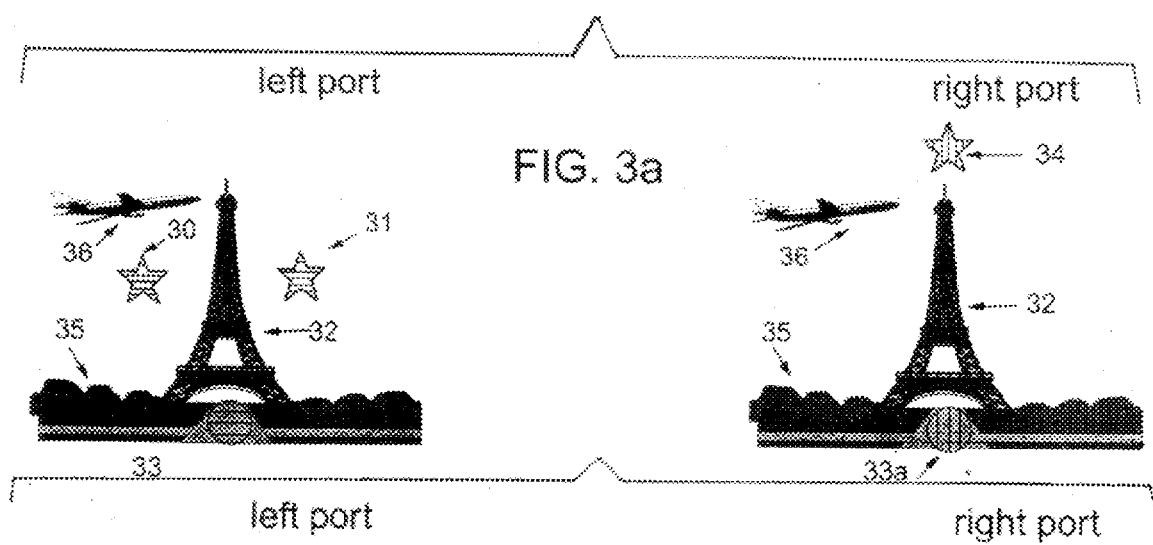
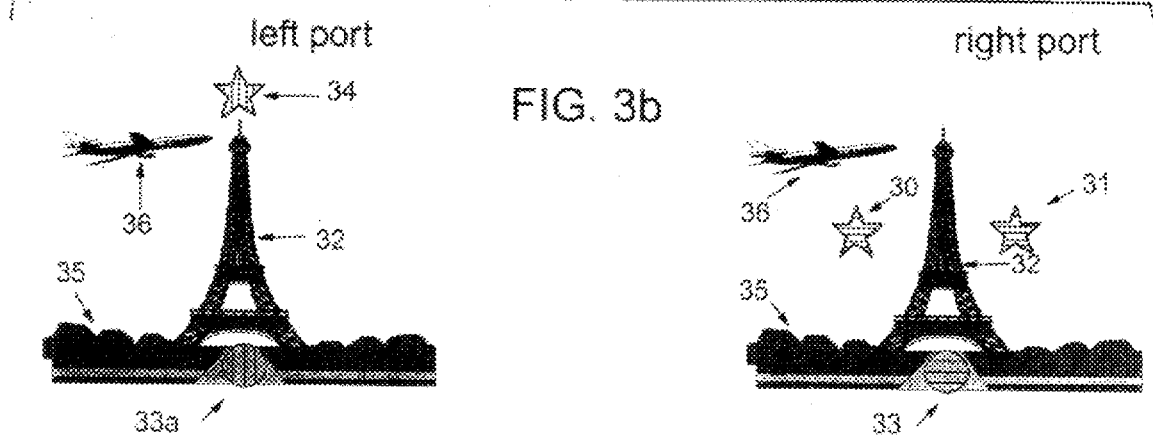

PORTABLE DEVICE FOR EVALUATION OF BINOCULAR VISION PROBLEMS

FIELD OF THE INVENTION

This invention relates to testing devices and procedures for measuring the vision parameters of stereoscopic vision, fusion and fusion recovery, and particularly those utilizing the Worth 4-Dot test.

BACKGROUND OF THE INVENTION

Stereoscopic vision, fusion (single binocular vision) and fusion recovery are various aspects of normal eye operation which affect depth perception and the extent to which eyes of a human visual system operate in normal tandem. Measurements of the extent a particular person's visual system actually deviates from the norm in such aspects, have been effected for many years by means of the "Worth 4 Dot" test. This test consists of four lights of varying colors arranged in a diamond configuration. Two lights (designated A) are green, one (designated light B) is red and the fourth light (designated light C) is white. In conducting the test, the patient wears a pair of glasses with a red filter before one eye and a green filter before the other eye (the two filters are of complementary colors and the same colors as the colored lights). When fusion is present (normal binocular vision) four lights are seen, two green (by the eye behind the green filter), one red (by the eye behind the red filter), and the white light, seen by both eyes, appears to be a mixture of red and green. White light C, seen by both eyes, can normally alternate between red, green and white as the visual system of the patient continuously samples the input and tries to resolve the abnormal condition of viewing dissimilar images with corresponding points in the two eyes.

In the human visual system, for every point or location in one eye there is a point in the other eye which corresponds exactly, for viewing. When the eyes are not precisely aligned, different images fall on the corresponding points of the two eyes with resultant double vision. The Worth 4-Dot test is used to detect this condition, wherein one dot (light C) is presented as red to one eye and as green to the corresponding point in the other eye, with the two corresponding pair of points seeing the same image but in different colors. With normal vision, a competition called retinal rivalry results. With double vision such rivalry does not occur since the light C of the Worth 4-Dot test does not stimulate corresponding retinal elements.

If the visual system is affected by a condition that impairs or delays the nerve inputs from one eye which are destined for binocular sensitive neurons in the visual cortex, the input from the impaired side will arrive late and will not be recognized by the visual cortex. Patients having impaired visual input from one eye ("bad eye") will see the white light C in the color of the filter in front of the "good" eye. By reducing the light intensity with a neutral density filter to one eye, the speed of the impulses traveling from that eye is reduced. Thus, a neutral density filter placed before the "good" eye will reduce the speed of the impulses transmitted from that eye. By increasing the density of the filter, the speed of the impulses travelling from the "good" eye can be reduced to below the velocity of the impulses coming from the "bad" eye. As a result "bad" eyes are identified with the color of the white light changing from that of the filter before the "good" eye to the color of the filter before the "bad" eye. The extent of sensory impairment is measured by correlation to the extent of filter density change.

Current techniques for utilizing the Worth 4-Dot testing procedure involve requiring the subject or patient to wear spectacles having one red and one green filter over corrective lenses while the examiner holds a Worth 4-Dot flashlight and applies individual neutral density filters over one eye of the patient, all in a semi-darkened room.

SUMMARY OF THE INVENTION

It is an object of the present invention to provide a simplified device for administering the Worth 4-Dot test, without flashlights and regardless of room lighting conditions.

It is a further object of the present invention to provide such device wherein it provides measurements of the three vision parameters of stereoscopic vision, fusion and fusion recovery.

It is yet another object of the present invention to provide such device as a modification of an existing commercially available photograph viewing device.

These and other objects, features, and advantages of the present invention will become more evident from the following discussion and drawings in which:

SHORT DESCRIPTION OF THE DRAWINGS

FIGS. 3a and 3b show the slide figures of FIG. 2 as arranged for the two View Master viewers used in accordance with the present invention;

DETAILED DESCRIPTION OF THE INVENTION

Figure 1:
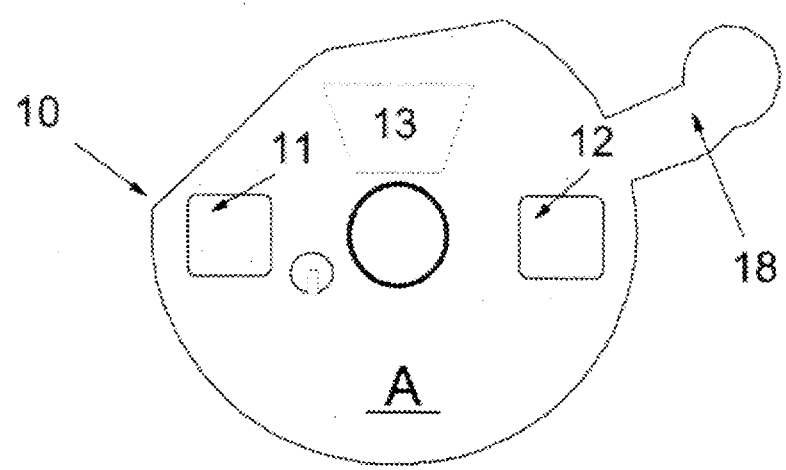
FIG. 1 is a prior art View Master® slide holder or photograph viewer.

The present invention comprises a stereo slide viewer, e.g., a hand held slide viewer, commercially available under the trademark View Master, which is adapted for successive binocular viewing of a series of mounted slides. Two viewers are utilized for separately testing the right and left eyes. One slide viewer is adapted for testing one eye and the other slide viewer is adapted for testing the other eye. These slide viewers each have eyepieces for viewing by both eyes simultaneously (binocular viewing) of normally, the same image, in the form of two slide images directly positioned in front of each of the eyes. The viewers each have either a translucent or transparent opening behind the slides, for positioning in front of a light source for illumination or alternatively for light from a self contained illumination source. The slides in such viewers are mounted in a circular reel or disc such that the identical images appear before the left and right eyes. Mechanical advancement of the reel (usually with a lever driven mechanism), changes the slide-images which appear before the respective eyes by rotation of the slide.

In accordance with the present invention, the slide viewers are modified to constantly maintain fixed-position similar images before each of the eyes at all times. These images are similar but not identical in that "4-Dot" type segments, of the images before the left and right eyes, differ in color and/or positional image segment placement on the images.

The mounted slides on the reels which are moved, comprise neutral density filters of known varying filtering intensity. These filters are thereby superimposed on the fixed position images to vary the speed of impulses from the eye. Each filter is stereo paired with a complete transparency or simple opening, whereby only a specific eye is affected by the change in density of the filter. The viewer may also be modified to retain additional filters, if desired, before the eyepiece corresponding to the specific eye. The left and right eyepieces of each of the slide viewers are provided with the transposed images of the images before the left and right eyepieces of the other slide viewer, i.e., the image before the left eye in one viewer is before the right eye in the other viewer and vice versa. Mounting of the different densities of the neutral density filters, used in the two viewers respectively, is reversed, in the reels used in each of the viewers, in correspondence with the change of eyes being tested and reversal of the images.

In accordance with a preferred embodiment of the present invention, colored transparencies of "4-Dot" test image pairs are mounted over the two ports of a lighted View-Master. The "4-Dot" test pairs comprise: (1) images that encourage fusion; (2) images which are stereoscopic cues; (3) images which are viewed by one of the eyes (the right eye in a first viewer and the left eye in the other viewer); (4) images viewed only by the opposite eye (the left eye in the first viewer and the right eye in the other viewer); (5) and an image viewable by both eyes, of the same shape and in the same position but of different color.

Specifically, images that encourage fusion include those which are background items which are identical in color, shape, size and position in both members of the image pair. Images which are stereoscopic cues are those items which are identical in color, shape and size but which are off-set horizontally in one member of the image-pair, thereby creating a 3D or stereoscopic effect to the image. This image in the third dimension adds to the ability to test for stereopsis.

The images which are viewed by one eye or the opposite eye in each of the viewers are the 4-Dot test images such as dots, stars, and the like, of the same or different colors and in the same or different position, with the requirement that the shape and position of one of the images, but not the color, must be identical in both members of a stereo pair (viewable by both eyes).

DETAILED DESCRIPTION OF THE DRAWINGS AND THE PREFERRED EMBODIMENT

Figure 4A:
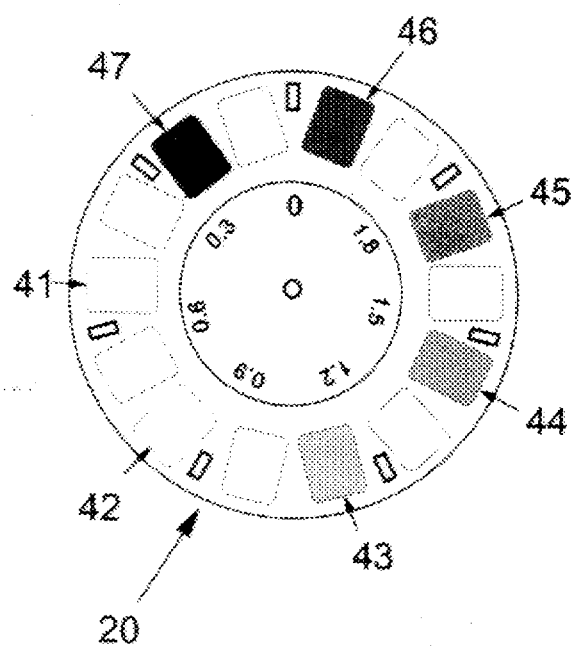
FIGS. 4a and 4b depict the graded series of neutral density filters in a View Master reel mount, as used with the slide viewers having the slide figures of FIGS. 3a and 3b respectively.
Figure 4B:
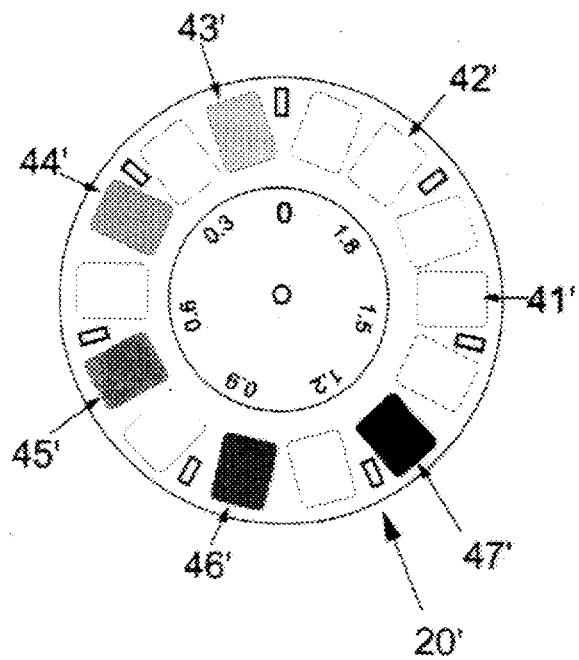

With reference to the drawings, a prior art View-Master® type slide viewer 10 is depicted from the viewing side A, with left eye viewing port 11 and right eye viewing port 12. Information port 13, provides information from an inserted slide reel regarding the slide being viewed. In normal prior art use, the slide reel, such as slide reels 20 and 20' shown in FIGS. 4a and 4b, is provided with identical slide pictures at each opposing set of positions, for stereo viewing of a slide image, usually a photograph transparency. Lever 18 is adapted to engage and rotate the inserted slide reel for viewing of successive images (identical image pairs). Illumination of the slide images is effected with backlighting by either a translucent window behind the slide image which is juxtaposed with an external constant level light source (the sun, a lamp, etc.), or by means of an internal light source (e.g., battery powered bulb).

Figure 2:
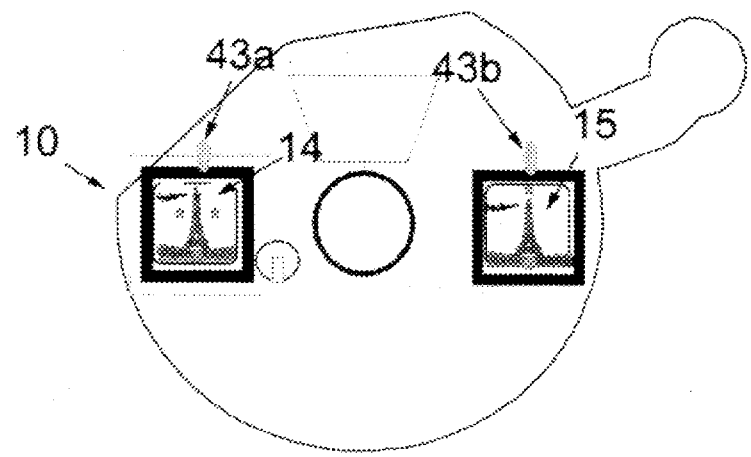
FIG. 2 is the View Master viewer of FIG. 1, having slide figures affixed to each of the right and left eye viewing areas, differing with "Worth 4-Dot" differences in the form of different placement and colors of the stars and different colors of the dots as shown.

In accordance with the present invention and for the various tests, one or two viewers are utilized in the test procedure (one for testing for each of the right and left eyes separately). For simplicity (and since the viewers differ only with reversal of the position of the fixed images as shown in FIGS. 3a and 3b) only one of the two viewers is shown in FIG. 2. Stereo viewable image transparencies or slides 14 and 15 are, in contrast to prior art photograph viewing use, fixed into non-movable position in each of eye ports 11 and 12 respectively of viewer 10. The slide reel 20, shown in FIG. 4a, used with viewer 10, is provided with a series of neutral density filters which are used to selectively reduce the level of the back-lighting illumination to the fixed position test image pairs. Lever 18 is used to change the filter and thus to vary the intensity of illumination reaching the image transparencies 14 and/or 15. The second slide viewer (not shown) differs from the first only in that the positions of slides 14 and 15 are transposed (FIG. 3b), with respect to the viewing eyes, and slide reel 20' (FIG. 4b) is used therewith.

In accordance with the present invention, the stereo image pairs 14 and 15, shown in greater detail in FIGS. 3a and 3b, in their respective relation to the viewing eyes (image 14 is before the left eye in the viewer using the arrangement of FIG. 3a and image 15 is before the right eye and transposed in FIG. 3b), differ with respect to the stars and the color of the respective dots. Thus, image 14 has two stars 30 and 31 flanking the Eiffel Tower 32 and a dot 33 at the base thereof (the stars and dot are colored blue, as indicated). Image 15 has one star 34 above the tower and one dot 33a at the base thereof in the same position as in image 14 but both the star 34 and the dot 33a are colored red, as indicated. In the images 14 and 15, the tower 32 and landscaping 35 are background items which encourage fusion, the airplane 36 is in the third dimension and functions as a stereoscopic cue. Shapes A (stars) and shape B (dots) are arranged in images 14 and 15 as images that are viewed by one of the eyes (the left eye with the images of FIG. 3a and the right eye of FIG. 3b) in image 14 of the blue stars 30 and 31 (shape A) at the 3:00 and 9:00 meridian and the blue dot 33 at the 6:00 meridian. Corresponding images viewed by the opposite eye (the right eye with the images of FIG. 3a and the left eye with the images of FIG. 3b) are the shape A red star 34 at the 12:00 meridian and the shape B red dot 33a at the 6:00 meridian. Though the shape and position of the shape B items are identical they differ in color. As shown, right eye defects are measured with the viewer 10 having the image arrangement of FIG. 3a and the slide filter reel 20. Left eye defects are measured with the viewer 10 having the image arrangement of FIG. 3b and the slide filter reel 20'. As an example of preparation of the slide filter reel mounts 20 and 20' of FIGS. 4a and 4b, Kodak Wratten gelatin filters are cut to size from commercial sheets. The FIGS. 4a and 4b exemplify the use of a filter series 41–47 and 41'–47' respectively of 0.0, 0.3, 0.6, 0.9, 1.2, 1.5, and 1.8, though any other suitable arrangement is possible. With the reel mount 20 and 20', for commercially available viewers, a series of seven different filters are possible on the reel. As shown, the filters are mounted in each of reels 20 and 20' so that the filter density increases as the reels advance in a clockwise direction. The filters operate by cutting down the amount of external or internal illumination on the transparencies with concomitant measurable slowing of the speed of the impulses from the viewing eye. If desired, additional filters can be placed in front of one of the eyepieces to extend the range of the neutral density filter scale, such as hanging from hooks 43a and 43b.

With the device of the present invention it is possible, with a hand held stereo viewer, independently of an external light source or colored filter spectacles, to measure fusion recovery by simply advancing a reel containing filter slides. Identification of which eye or optic nerve has a defect is made possible by use of the eye specific (right or left) testing viewers. Additionally, in contrast to the standard Worth 4-dot tests, the device tests for stereopsis in addition to fusion.

TESTING PROTOCOL

In accordance with the present invention and with use of the device described herein (viewer #1 for right eye tests and viewer #2 for left eye tests) the following procedure is utilized in detecting defects in specific eyes:

The subject is instructed to hold viewer #1 and to look at the image while keeping both eyes open, with the following sequence of questions and instructions:

1) How many towers and how many airplanes do you see?

2) Is the position of the airplane in front of or behind the tower?

3) How many red and blue stars do you see?

4) What color is the solid circle beneath the tower?

5) Advance the reel until the circle is the same red as the red star.

With normal eyes the answers to the above questions, using both viewers #1 and #2, are:

1) One tower and one airplane;

2) The airplane is behind the tower;

3) One red star and two blue stars;

4) Red or both red and blue;

5) Either the circle and star are the same color (initially) or the lever is advanced and the filter density at which the star and circle are the same color is checked for each of the viewers and the values agree within a set standard.

With eyes exhibiting lack of fusion the answers for viewer #1 are:

1) One tower and one airplane;

2) I can't tell;

3) One red star or two blue stars;

The examiner determines the fixating eye from the answer to question #3. The answer to question #3 is one red star if the right eye is the fixating eye and two blue stars if the left eye is the fixating eye (these answers are with use of viewer #1 and the reverse with use of viewer #2).

With mal-aligned eyes, when the subject cannot maintain fusion but has binocular vision, i.e., sees double double, the answers are the same for viewers #1 and #2:

1) Two towers and two airplanes.

The examiner has the choice of correcting the diplopia by adding prisms or terminating the test.

With a defect in the right eye and using viewer #1:

1) One tower, one airplane;

2) The airplane is behind the tower;

3) One red star and two blue stars;

4) Blue;

5) The lever is advanced until the red star and circle appear the same color.

The examiner records the filter density, and, if necessary, additional neutral density filters are externally placed in front of the left eye piece and the testing is repeated. The readings with viewer #1 is the optical density of the filter need to balance the defect in the right eye. The test is repeated using the viewer #2 and the subject should see the circle as red.

With a defect in the left eye and using viewer #1:

1) One tower and one airplane;

2) The airplane is behind the tower;

3) One red star and two blue stars;

4) Red

Using viewer #2:

1) One tower and one airplane;

2) The airplane is behind the tower;

3) One red star and two blue stars;

4) Blue;

5) The lever is advanced until the red star and circle appear the same color.

The examiner records the filter density representing the optical density needed to balance the defect in the left eye, and if the densest filter is insufficient, additional neutral density filters may be externally placed as described above.

It is understood that the above description and drawings, as well as the exemplified test protocol questions and answers are illustrative in nature and details contained therein are not to be construed as limitations on the present invention. Changes in viewer structure, components, images and procedures are possible without departing from the scope of the present invention as defined in the following claims.

What is claimed is:

1. A portable device for use in testing eyes for binocular vision problems, wherein the device comprises an image viewer having separate left and right eye viewing means, wherein an image is fixed in place in each of the left and right eye viewing means, the device further comprising a single illumination means for illumination of the image relative to each viewing eye and wherein images fixed in each of the left and right eye viewing means are substantially the same but wherein a similarly shaped and positioned defined segment in each image differs in complementary colors between images for direct viewing by each of the left and right eyes.

2. The device of claim 1, wherein the images viewable by each of the left and right eyes further vary with respect to segments in each, which differ in position and one or more of color and number.

3. The device of claim 1, wherein two different recognizable items appear identically in each of the images and are in the same relative position relation to each other in each of the images.

4. The device of claim 3, wherein the images comprise identical backgrounds which encourage fusion and wherein the two recognizable items comprises images which provide stereoscopic cues.

5. The device of claim 4, wherein an image viewable by one eye comprises at least one segment not in the image viewable by the other eye.

6. The device of claim 5, wherein segments viewable together by normal eyes comprise four segments, with two of the segments being viewable by one eye and one of the segments viewable by the other eye, and with a fourth segment being viewable by both eyes together, and wherein the fourth segment, viewable by each eye, is of a different complementary color from the corresponding fourth segment viewable by other of the eyes.

7. The device of claim 6, wherein the device comprises means for varying the intensity of the illuminated image which reaches one of the left or right eye.

8. The device of claim 7, wherein said device comprises a slide viewer adapted for viewing of a series of identical slide pairs, said slide viewer further comprising advancing means for changing slide pairs viewable by the left and right eyes and wherein said slide pairs comprise at least one neutral density filter with which light illuminating one fixed image is made to be of lower intensity than light illuminating the other fixed image, and wherein the series of slide pairs comprises neutral density filters of varying densities.

9. The device of claim 8, wherein the viewer comprises means for utilizing an external light source for the illuminating of the images.

10. The device of claim 8, wherein the viewer comprises internally contained illumination means.

11. The device of claim 8, wherein said device further comprises means for placement and support of at least one neutral density filter in a position between the fixed image and a viewing eye.

12. A set of devices for testing both and left and right eyes of a patient comprising two viewing devices according to claim 8, wherein a first viewing device is used for testing fusion and fusion recovery of a first eye and wherein a second viewing device is used for testing fusion and fusion recovery of the other eye, wherein the first device has a first image fixed in the viewing means for the first eye being tested and a second image fixed in the viewing means for the second eye and wherein the other viewing device has said first image fixed in the viewing means of the second eye being tested and said second image fixed in the viewing means for the first eye, and wherein the neutral density filters in each of the first and second viewing devices are positioned to selectively reduce illumination of the image being viewed by the eye not being tested respectively.

* * * * *